(12) United States Patent
Yang et al.

(10) Patent No.: US 11,109,781 B2
(45) Date of Patent: Sep. 7, 2021

(54) ARRAYED WAVEGUIDE GRATING (AWG)-BASED RAMAN SPECTROSCOPY FOR GLUCOSE MONITORING

(71) Applicants: Sheng Yang, San Francisco, CA (US); Yen-Chun Yeh, Menlo Park, CA (US); Dominik Schmidt, Los Altos, CA (US)

(72) Inventors: Sheng Yang, San Francisco, CA (US); Yen-Chun Yeh, Menlo Park, CA (US); Dominik Schmidt, Los Altos, CA (US)

( * ) Notice: Subject to any disclaimer, the term of this patent is extended or adjusted under 35 U.S.C. 154(b) by 207 days.

(21) Appl. No.: 15/890,206

(22) Filed: Feb. 6, 2018

(65) Prior Publication Data

US 2018/0228411 A1    Aug. 16, 2018

Related U.S. Application Data

(60) Provisional application No. 62/457,646, filed on Feb. 10, 2017.

(51) Int. Cl.
*A61B 5/1455* (2006.01)
*G02B 6/136* (2006.01)
*G02B 6/42* (2006.01)
*G01J 3/44* (2006.01)
*G01J 3/18* (2006.01)
(Continued)

(52) U.S. Cl.
CPC ........ *A61B 5/1455* (2013.01); *A61B 5/14532* (2013.01); *G01J 3/0256* (2013.01); *G01J 3/1895* (2013.01); *G01J 3/44* (2013.01); *G01N 21/65* (2013.01); *G02B 6/12002* (2013.01); *G02B 6/12004* (2013.01); *G02B 6/12014* (2013.01); *G02B 6/136* (2013.01); *G02B 6/4214* (2013.01); *G02B 6/4298* (2013.01); *A61B 5/0075* (2013.01); *A61B 2562/0242* (2013.01); *A61B 2562/12* (2013.01); *G01J 2003/282* (2013.01)

(58) Field of Classification Search
None
See application file for complete search history.

(56) References Cited

U.S. PATENT DOCUMENTS

2014/0185042 A1*  7/2014  Baets ............... G01N 21/658
356/301

OTHER PUBLICATIONS

Sensors and Actuators B: Chemical. Papers 60(1), 19-26,1999. (2 pgs).

(Continued)

*Primary Examiner* — Eric F Winakur
*Assistant Examiner* — Marjan Fardanesh
(74) *Attorney, Agent, or Firm* — Strong & Hanni, P.C.; Joseph Shapiro

(57) ABSTRACT

Various embodiments of the invention provide systems and methods for low-cost, low-power Array Waveguide Grating (AWG)-based miniaturized Raman spectroscopy for use in non-invasive glucose monitoring systems, such as in wearable devices that require no replenishment of chemicals or enzymes. The AWG may be manufactured using VLSI processing technology, which significantly reduces manufacturing cost and replaces holographic grating as the dispersive component of light. In embodiments, the AWG is integrated with a number of PIN photodiode detectors on a substrate to further reduce cost and signal loss. In embodiments, a prism-coupling method eliminates alignment problems associated with traditional approaches that utilize fiber-coupling methods.

12 Claims, 7 Drawing Sheets

(51) Int. Cl.
*A61B 5/145* (2006.01)
*G01N 21/65* (2006.01)
*G02B 6/12* (2006.01)
*G01J 3/02* (2006.01)
*A61B 5/00* (2006.01)
*G01J 3/28* (2006.01)

(56) References Cited

OTHER PUBLICATIONS

Lee et al.,"Glucose measurements with sensors and ultrasound," Ultrasound Med Biol. Papers 31(7), 971-977, 2005. (2 pgs).
Schrader et al."Non-invasive glucose determination in the human eye," J. Mol. Struct. Papers 735-736, 299-306, 2005. (2 pgs).
Martin et al.,"Using two discrete frequencies within the middle infrared to quantitatively determine glucose in serum," J. Biomed. Opt. Papers 7(4), 613-617, 2002. (1 pg).
Chaiken et al., "Effect of hemoglobin concentration variation on the accuracy & precision of glucose analysis using tissue modulated, noninvasive, in vivo Raman spectroscopy of human blood: a small clinical study," J. Biomed. Opt. Papers 10(3), 031111, 2005. (2 pgs).
Vashist et al., "Non-invasive glucose monitoring technology in diabetes management: A review," Anal. Chim. Acta. Papers 750, 16-27, 2012. (1 pg).
Lyandres et al.,"Progress Toward an In Vivo Surface-Enhanced Raman Spectroscopy Glucose Sensor," Diabetes. Technol. Ther. Papers 10(4), 257-265, 2008. (18 pgs).
Berger et al.,"Multicomponent blood analysis by nearinfrared Raman spectroscopy," Appl. Opt. Papers 38(13), 2916-2926, 1999. (11 pgs).
Ismail et al.,"Raman spectroscopy with an integrated arrayed-waveguide grating," Opt. Lett. Papers 36(23), 4629-4631, 2011. (4 pgs).
Magnusson & Wang,"New principles for optical filters," Appl. Phys. Lett, Papers 61, 1022-1024, 1992. (4 pgs).
Vonach et al.,"Application of mid-infrared transmission spectrometry to the direct determination of glucose in whole blood," Applied Spectroscopy, Paper 52, 820-822,1998. 2pgs.
Planck et al.,"The Theory of Heat Radiation," Dover Publications, New York (1914). [online], [Retrieved Nov. 6, 2019]. Retrieved from Internet <URL: https://www.gutenberg.org/files/40030/40030-pdf.pdf> (14pgs).
Election/Restriction Requirement dated Oct. 8, 2019, in related U.S. Appl. No. 15/890,179. (6 pgs).
Resposonse filed Nov. 6, 2019, in related U.S. Appl. No. 15/890,179. (7 pgs).
Yanga et al.,"Single chip AWG-based Raman spectroscopy for continuous glucose monitoring," In Optical Diagnostics and Sensing XVI: Toward Point-of-Care Diagnostics, Proceedings of a meeting held Feb. 15-16, 2016. (6 pgs).
Zhang et al.,"Global healthcare expenditure on diabetes for 2010 and 2030," Diabetes Res Clin Pract. Papers 87(3), 293-301, 2010. (2 pgs).
Kurnik et al.,"Application of the Mixtures of Experts algorithm for signal processing in a noninvasive glucose monitoring system,".
Yeh et al.,"Self-emission glucose monitoring system with single chip guided-mode resonance filters," In Optical Diagnostics and Sensing XVI: Toward Point-of-Care Diagnostics, Proceedings of a meeting held Feb. 15-16, 2016. (5 pgs).
Nelson et al.,"Development and validation of a multiwavelength spatial domain near-infrared oximeter to detect cerebral hypoxia-ischemia," Journal of Biomedical Optics 11(6), 2006. (8 pgs).
Shen et al.,"The use of Fournier-transform infrared spectroscopy for the quantitative determination of glucose concentration in whole blood," Phys Med Biol, Paper 48, 2023-2032, 2003. (3 pgs).
Enejder et al.,"Raman spectroscopy for non-invasive glucose measurements," Journal of Biomedical Optics, Paper 10, 031114, 2005. (9 pgs).
Malchoff et al.,"A novel noninvasive blood glucose monitor," Diabetes Care, Paper 25, 2668-2275, 2002. (9 pgs).
Wang et al.,"Theory and application of guided mode resonance filters," Appl. Phys. Lett, Papers 32, 2606-2613, 1993. (1 pg).
Shin et al.,"Thin-film optical filters with diffractive elements and waveguides," Opt. Eng., Paper 37(9), 2634-2646, 1998. (5 pgs).

* cited by examiner

200

ARRAYED WAVEGUIDE GRATING (AWG)-BASED RAMAN SPECTROSCOPY FOR GLUCOSE MONITORING

CROSS REFERENCE TO RELATED PATENT APPLICATIONS

The present application claims priority to U.S. Provisional Application Ser. No. 62/457,646, titled "Arrayed Waveguide Grating (AWG)-Based Raman Spectroscopy for Glucose Monitoring," filed on Feb. 10, 2017 and naming as inventors, Sheng Yang, Yen-Chun Yeh, and Dominik J. Schmidt, which application is incorporated herein by reference as to its entire content.

BACKGROUND

A. Technical Field

The present disclosure relates to diagnostic sensor systems. More particularly, the present disclosure related to systems and methods for monitoring blood glucose levels using optical measuring devices.

B. Description of the Related Art

According to a recent estimate of the World Health Organization, 366 million people worldwide will be suffering from diabetes by the year 2030. The increasing frequency of diabetes incidences has led to serious concerns over related health issues and has created a vast market for self-monitoring blood glucose devices. Commercially available blood glucose measurement devices typically require patients to extract blood from a finger by using an automatic lancet to puncture the finger in order to extract a drop of blood that is collected on a disposable test strip. The strip is then inserted into the blood glucose measurement device that utilizes an enzyme electrochemical glucose sensor to perform a chemical analysis to determine the patient's current blood glucose level. This procedure is not only inconvenient for diabetes patients but may also unnecessarily inflict pain on the user.

Various non-invasive glucose monitoring (NGM) technologies, including reverse inotoporesis, sonophoresis, thermal emission spectroscopy, absorbance spectroscopy, and Raman spectroscopy, have been evaluated in the hope of filling a market need for improved glucose monitoring products. While each approach has its own advantages and disadvantages, techniques that utilize Raman spectrometry stand out due their ability to provide detailed information about chemical compositions, including protein, lipid, skin, and interstitial fluid despite operating on relatively weak input signals.

As possible solutions, different kinds of Raman spectrometric techniques have been introduced to improve signal intensity, including tissue modulation and surface-enhanced Raman spectroscopy. However, existing proposals for using Raman spectrometry in an NGM device suffer from numerous drawbacks, including high power consumption, large size, high manufacturing cost, and the need to regularly replenish chemicals or enzymes. These restrictions make the existing proposals impracticable for daily use.

More recent research has targeted some of the well-known problems by investigating arrayed waveguide gratings (AWGs) for use in Raman spectrometry. AWGs are silicon-based planar lightwave circuits that are widely used in optical multiplexers and demultiplexers, e.g., in wavelength division multiplexing systems. While most commercial AWG products operate at wavelengths in the range from 1530 nm to 1560 nm, if properly designed, AWGs may also disperse light efficiently in the Raman signal range, e.g., from 800 nm to 900 nm. A major problem of existing AWGs, however, is light-coupling to the ends of an AWG device, which is facilitated by optical fibers that are connected to input and output ports of the AWG device. Since waveguide dimensions are on the order of micrometers, alignment between optical fibers and the AWG require highly specialized instrumentation, such as a laser welding automatic alignment system. This not only greatly increases cost but also makes the alignment process very time-consuming.

Accordingly, what is needed are low-cost and efficient systems and methods that take advantage of Raman spectrometry to provide non-invasive glucose monitoring.

BRIEF DESCRIPTION OF THE DRAWINGS

References will be made to embodiments of the invention, examples of which may be illustrated in the accompanying figures. These figures are intended to be illustrative, not limiting. Although the invention is generally described in the context of these embodiments, it should be understood that it is not intended to limit the scope of the invention to these particular embodiments.

FIGURE ("FIG.") 1 illustrates a simplified schematic of an exemplary micro-Raman spectrometer system utilizing an AWG chip, according to various embodiments of the present disclosure.

DETAILED DESCRIPTION OF THE PREFERRED EMBODIMENTS

Figure 1:
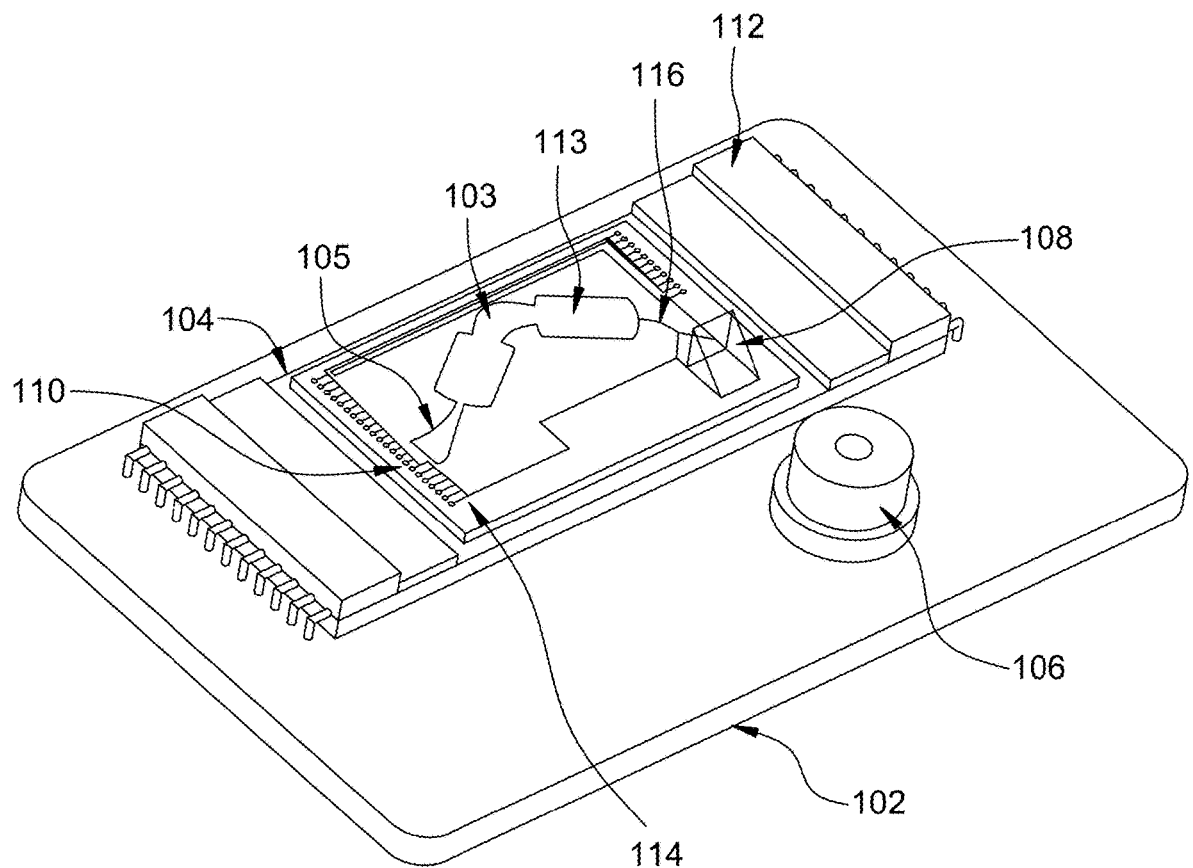

In the following description, for purposes of explanation, specific details are set forth in order to provide an understanding of the invention. It will be apparent, however, to one skilled in the art that the invention can be practiced without these details. Furthermore, one skilled in the art will recognize that embodiments of the present invention, described below, may be implemented in a variety of ways, such as a process, an apparatus, a system, a device, or a method on a tangible computer-readable medium.

Components, or modules, shown in diagrams are illustrative of exemplary embodiments of the invention and are meant to avoid obscuring the invention. It shall also be understood that throughout this discussion that components may be described as separate functional units, which may comprise sub-units, but those skilled in the art will recognize that various components, or portions thereof, may be divided into separate components or may be integrated together, including integrated within a single system or component. It should be noted that functions or operations discussed herein may be implemented as components. Components may be implemented in software, hardware, or a combination thereof.

Furthermore, connections between components or systems within the figures are not intended to be limited to direct connections. Rather, data between these components may be modified, re-formatted, or otherwise changed by intermediary components. Also, additional or fewer connections may be used. It shall also be noted that the terms "coupled," "connected," or "communicatively coupled" shall be understood to include direct connections, indirect connections through one or more intermediary devices, and wireless connections.

Reference in the specification to "one embodiment," "preferred embodiment," "an embodiment," or "embodiments" means that a particular feature, structure, characteristic, or function described in connection with the embodiment is included in at least one embodiment of the invention and may be in more than one embodiment. Also, the appearances of the above-noted phrases in various places in the specification are not necessarily all referring to the same embodiment or embodiments.

The use of certain terms in various places in the specification is for illustration and should not be construed as limiting. A service, function, or resource is not limited to a single service, function, or resource; usage of these terms may refer to a grouping of related services, functions, or resources, which may be distributed or aggregated. Furthermore, the use of memory, database, information base, data store, tables, hardware, and the like may be used herein to refer to system component or components into which information may be entered or otherwise recorded.

Furthermore, it shall be noted that: (1) certain steps may optionally be performed; (2) steps may not be limited to the specific order set forth herein; (3) certain steps may be performed in different orders; and (4) certain steps may be done concurrently.

FIG. 1 illustrates a simplified schematic of an exemplary micro-Raman spectrometer system utilizing an AWG chip, according to various embodiments of the present disclosure. System 100 comprises PCB 102, AWG chip 104, laser source 106, coupling prism 108, PIN photodiodes 110, storage device 112, and aluminum pads 114. As depicted in FIG. 1, AWG chip 104, laser source 106, and storage device 112 may be disposed on PCB 102. AWG chip 104 comprises grating elements 103 (e.g., free propagation zones 113) and waveguides 105 (e.g., optical waveguides).

In embodiments, waveguides 105 may be optically coupled to laser source 106 that may be implemented as a TO-can packaged diode laser (e.g., 785 nm wavelength). Diode laser 106 may be used to shine light at a target (e.g., skin). Light 116 scattered off the skin may then be captured by prism 108 and directed toward waveguides 105 that guide the scattered light from prism 108 to grating elements 103. In embodiments, PIN photodiodes 110 may be coupled to storage device 112 that, in embodiments, comprises a current-input array ADC. It is understood that system 100 may comprise any number of additional optical and electrical components, such as lenses, optical filters, and signal processing devices to achieve the objectives of the present disclosure.

Unlike existing methods for detecting typically weak Raman signals associated with Raman spectroscopy that rely on CCD-based detectors and, if applied to AWGs, would result in unacceptably long integration times for accumulating sufficient photoelectrons, embodiments of the present disclosure utilize integrated PIN photodiode 110 to serve as a detector. In embodiments, PIN photodiode 110 may be placed at the output end of AWG 105. Advantageously, integration of photodiodes on the AWG substrate eliminates the complicated (e.g., waveguides are only a few microns in dimension) and expensive (commercial AWGs cost upward of $1,000) issues associated with fiber micro-alignment at the output of an AWG using off-chip detectors. In addition, by placing the detector at the end of each waveguide 105, photon loss is significantly reduced while greatly improving the amount of light signals that is transferred.

Since PIN photodiodes 110 themselves do not store photoelectrons, in embodiments, storage device 112 is used to provide capacitance onto which photoelectrons may accumulate. In embodiments, storage device 112 comprises a current-input array ADC (e.g., DDC232 by Texas Instruments) that may be used to read out current.

In embodiments, to eliminate alignment issues typically associated with fiber-coupling at an AWG input, a prism-coupling method is utilized to couple light into waveguides 105. This further minimizes complexity and eliminates cost associated with fiber-coupling micro-alignment.

In embodiments, AWG 105 disperses the light signals within a wavelength range from, e.g., 800 nm to 900 nm, that corresponds to the wavelength range of Raman scattering with respect to the wavelength (e.g., 785 nm) of the incident laser light (e.g., a monochromatic light beam) generated by laser 106.

One of skill in the art will appreciate that components of system 100 may be directly integrated into chip 102 or may be implemented on two or more separate chips.

Figure 2:
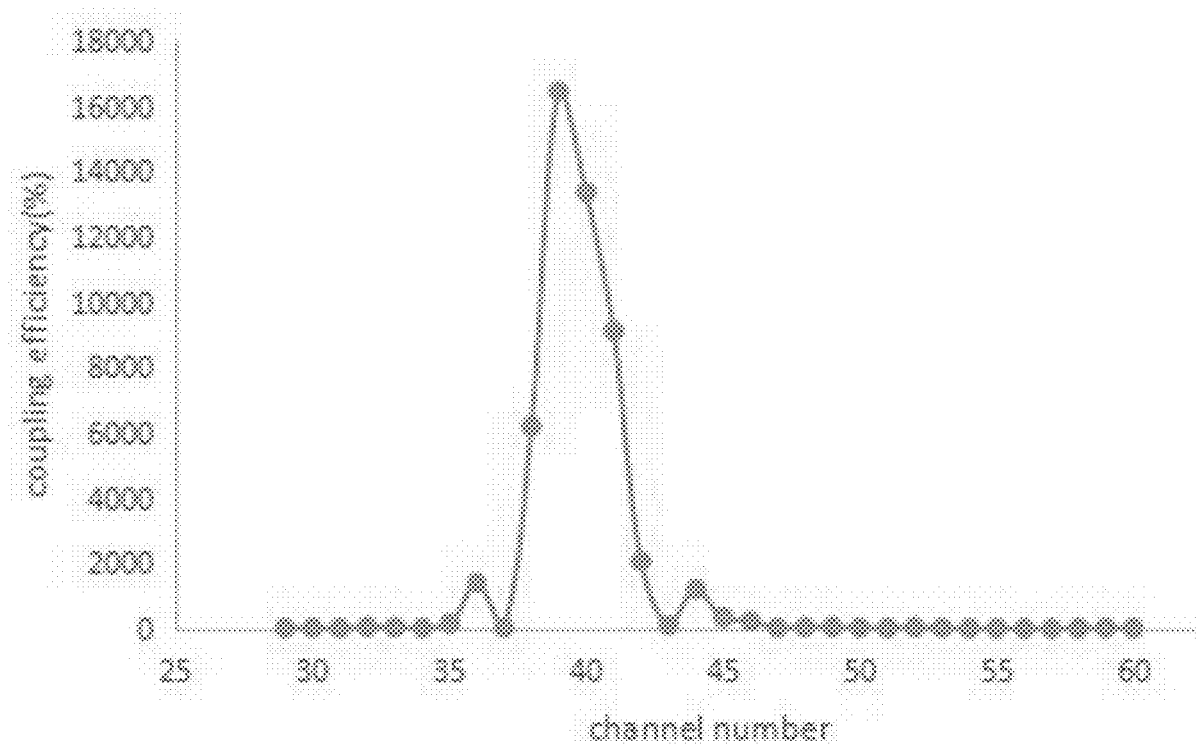
FIG. 2 is an exemplary diode laser characterization graph illustrating the effect of implementing a commercial AWG as grating and a PIN photodiode as detector into various embodiments of the present disclosure.

FIG. 2 is an exemplary diode laser characterization graph illustrating the effect embodiments of the present disclosure. It is noted that since currently no commercial AWG products are available that operate at the desired Raman spectrum range, a 32-channel AWG (OPLINK) was used to characterize an AWG's operating range from 1529.553 nm to 1554.134 nm using a 1550 nm diode laser (e.g., ML925B45F by Thorlabs) and a PIN photodiode (e.g., ETX100 by JDSU) as the detector. Laser characterization graph 200 in FIG. 2 has been obtained by implementing the 32-channel AWG as a grating and the PIN photodiode as a detector. Exemplary graph 200 is reconstructed from the data collected by the photodetector and shows an expected laser profile that can be observed, including side peaks that are characteristic for the diode laser. In embodiments of the present disclosure, an AWG having an operating range (e.g., 860 nm±16 nm) within the Raman spectrum range, may be similarly characterized and used.

Returning to FIG. 1, in embodiments, materials that are compatible with integrated circuit manufacturing (e.g., oxynitride) may be used to fabricate, for example, the core material for waveguide 105. It is understood that materials may undergo any type of semiconductor processing, such as chemical deposition or plasma enhanced chemical vapor deposition processes. In embodiments, in order to adjust one or more optical characteristics of the core material, the semiconductor processes may be adjusted accordingly. For example, the proportions of chemicals used in the fabrication process, such as the ratio of nitride to oxide, may be varied to achieve a desired refractive index for a particular material, for example, to adjust the refractive index for the deposited oxynitride layer to 1.512 at a wavelength of 850 nm.

It is known that in order to ensure high coupling efficiency, a prism having a refractive index higher than that of the core material of the waveguides is preferred, e.g., a rutile prism. However, rutile prisms (n=2.5086 at 850 nm) are relatively costly and, thus, not suitable with a low-cost design. Therefore, in embodiments, to facilitate a high coupling efficiency, coupling prism 108 may be made using, e.g., N-SF11 (n=1.7619 at 850 nm) or F2 (n=1.6068 at 850 nm).

Figure 3A:
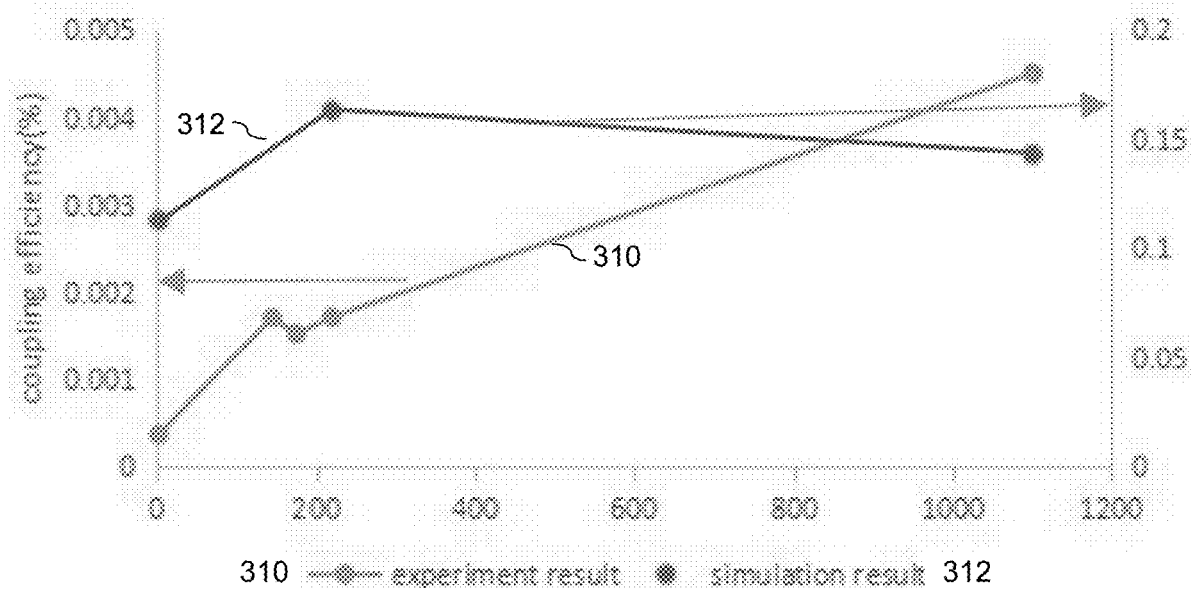
FIGS. 3A and 3B are exemplary graphs illustrating the effect of implementing prism-coupling according to various embodiments of the present disclosure.
Figure 3B:
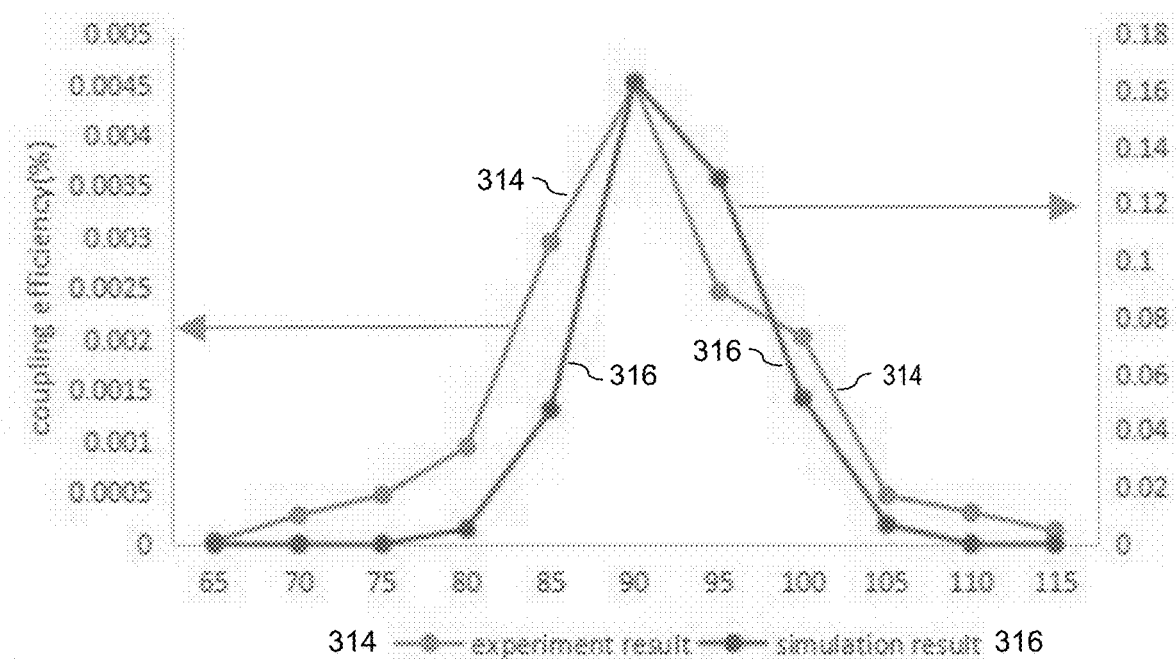

FIGS. 3A and 3B are exemplary graphs illustrating the effect of implementing prism-coupling according to various embodiments of the present disclosure. FIG. 3A illustrates the relationship between coupling efficiency and the thickness of the waveguide core. The characteristic curves in FIG. 3A have been obtained through experiments 310 and simulation results 312. To characterize prism-coupling, an F2 equilateral dispersive prism (e.g., PS850 by Thorlabs) was used in a first experiment. A laser beam was directed at the prism that was placed on glass samples having different thicknesses. A photodiode (e.g., Hamamatsu model S55971) was placed at the output end of the waveguide to serve as a detector. While, in theory, the optical intensity should not vary as the thickness of the waveguide decreases, optical intensity received at the detector decreased when the thickness of the glass waveguide samples decreased. Nevertheless, a considerable amount of light was successfully coupled into waveguides having a core thickness of 2 µm and a cladding thickness of 1 µm.

FIG. 3B illustrates the relationship between coupling efficiency and incident laser beam angle. In a second experiment that was conducted with a similar configuration as the first experiment, the impact of incident laser angle on the coupling efficiency was explored. As shown in FIG. 3B, the coupling efficiency was highest when the laser beam was directed at a 90-degree angle, centered at the middle of the base of the prism. It is noted that the measured coupling efficiencies 314 in FIGS. 3A and 3B are significantly lower than the theoretical or simulated coupling efficiencies 316. This may indicate that a significant portion of the radiation may have leaked at various interfaces of the measurement setup. It is noted that the use of, e.g., immersion oil may increase coupling efficiency.

The typical semiconductor process flow for the fabrication of waveguides on a chip starts with a silicon wafer onto which a guiding core and under-cladding layers are deposited. Then the patterns of the AWG core structure are defined by lithography and dry etch steps. Then, an overcladding layer may be formed, for example, by a hydrogen silsequioxane coating or PECVD silica deposition. This process flow is relatively simple. However, the resulting AWG core structure extends beyond the surface of the silicon wafer into a region in which, e.g., surface-mount electrical circuits may be located. As a result, the AWG is not embedded within the CMOS electrical circuitry, but rather is formed on top of silicon substrate.

Figure 4:
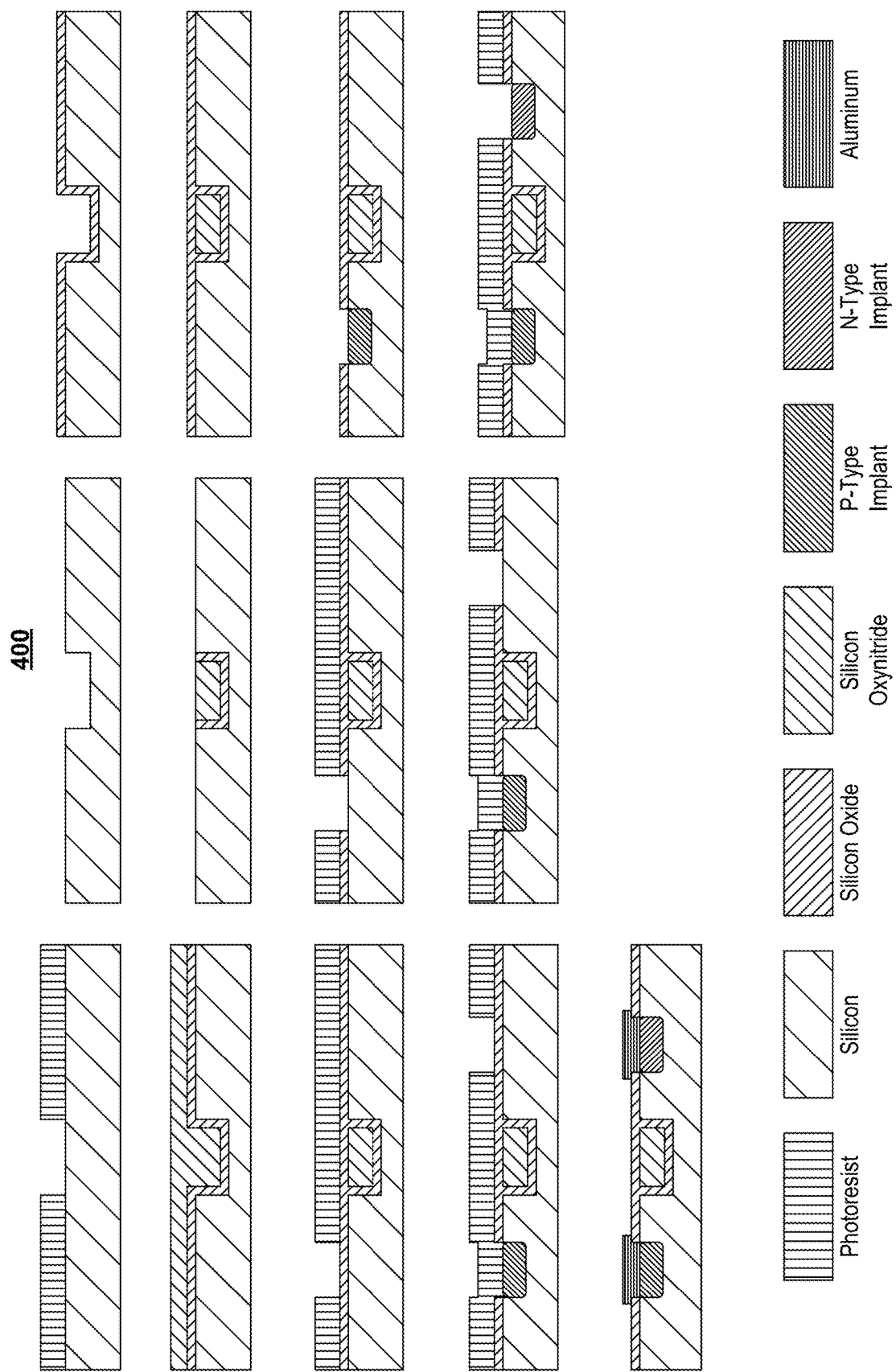
FIG. 4 illustrates an exemplary process flow for fabricating an integrated opto-electrical circuit that comprises an AWG and a PIN photodiode on the same plane on a chip.

In contrast, in various embodiments of the present disclosure, the AWG core material is embedded into the semiconductor substrate. In embodiments, the AWG and a detector are integrated into the same chip. FIG. 4 illustrates an exemplary process flow for fabricating an opto-electrical circuit that integrated an AWG and a PIN photodiode on the same plane on a chip. As shown in FIG. 4, in embodiments, waveguides having a guiding core and under-cladding material may be formed by filling trenches or gaps that have been etched into a substrate (e.g., silicon). FIG. 4 depicts 13 exemplary steps to produce the elements of an AWG, e.g., the waveguide denoted as silicon oxinitride, and elements of a PIN diode.

In embodiments, the PIN diode is formed by doped regions, labeled as p-type implant and n-type implant in FIG. 4 and an undoped region, e.g., silicon oxinitride. The doped regions of the substrate may be doped to any degree with n-type material (e.g., phosphorus atoms) and p-type material (e.g., boron atoms). In embodiments, the undoped region (e.g., silicon), which may also be an equally doped region having any desired width, may serve as the intrinsic region of the PIN diode. In embodiments, this intrinsic region forms a section of the waveguide core and, in operation, uses incident photons that have sufficiently high energy to create electron-hole pairs and, thus, enable a measurable current flow that then may be detected.

It is understood that not all processing steps are shown, e.g., not all photoresist stripping steps are shown. It is further understood that additional steps may be performed or modified to accomplish the objectives of the present disclosure.

Figure 5C:
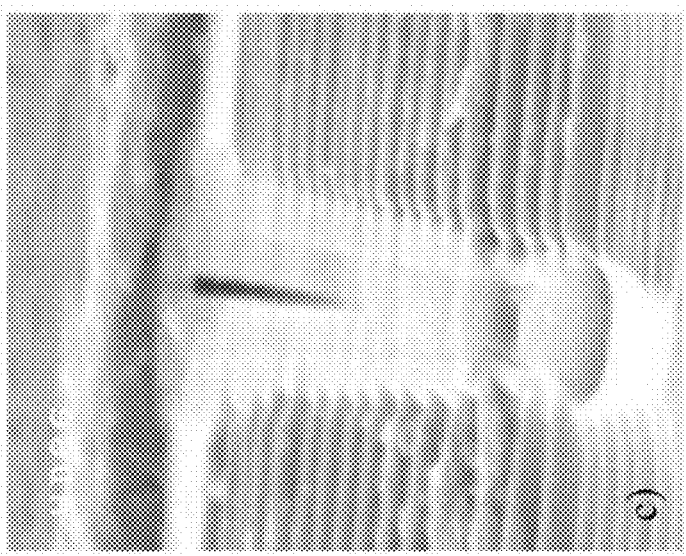
FIG. 5A-5C show SEM profiles of waveguides having varying feature sizes that have been manufactured by using the process flow shown in FIG. 4.
Figure 5B:
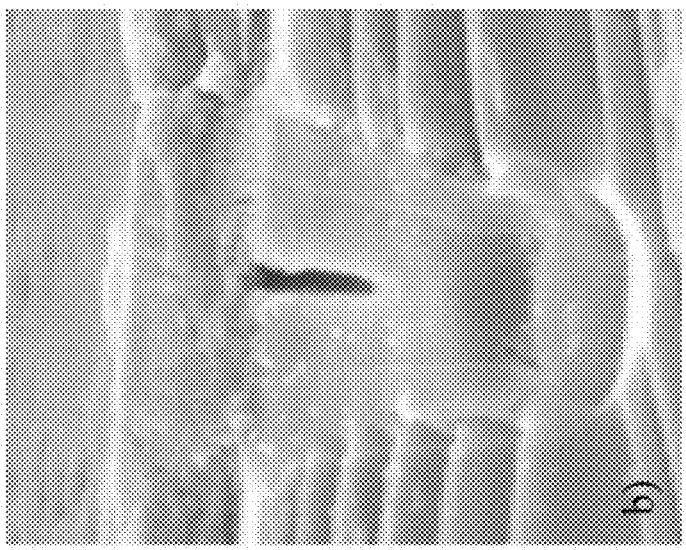
Figure 5A:
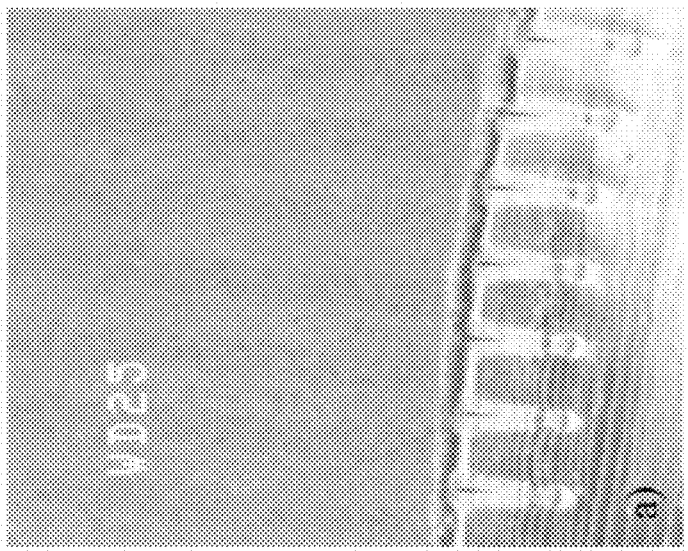

FIG. 5 shows SEM profiles of waveguides having varying feature sizes that have been manufactured by using the process flow shown in FIG. 4. FIG. 5A shows a waveguide array comprising waveguides having a 1.5 µm trench size. FIG. 5B shows a single waveguide having a trench size of 1.5 µm. FIG. 5C shows a single waveguide having a trench size of 3 µm. Trenches in FIG. 5A-5C are not entirely filled, which may occur, for example, when the openings of the trenches are relatively narrow, which may cause a void or seam to form within the core of the waveguides. Since imperfections may inhibit efficient propagation of light within the waveguides, especially in waveguides having many curvatures, such gap formation should be prevented. In embodiments, this may be accomplished by varying spatial dimensions, e.g., by relaxing the requirement for the aspect ratio of the trench depth to its width. In embodiments, a relatively wide waveguide width, e.g., 4.5 µm, may be used in a gapfill operation in order to produce seamless AWGs. Other solutions may involve the use of precursor materials and any other technique known in the art.

Figure 6:
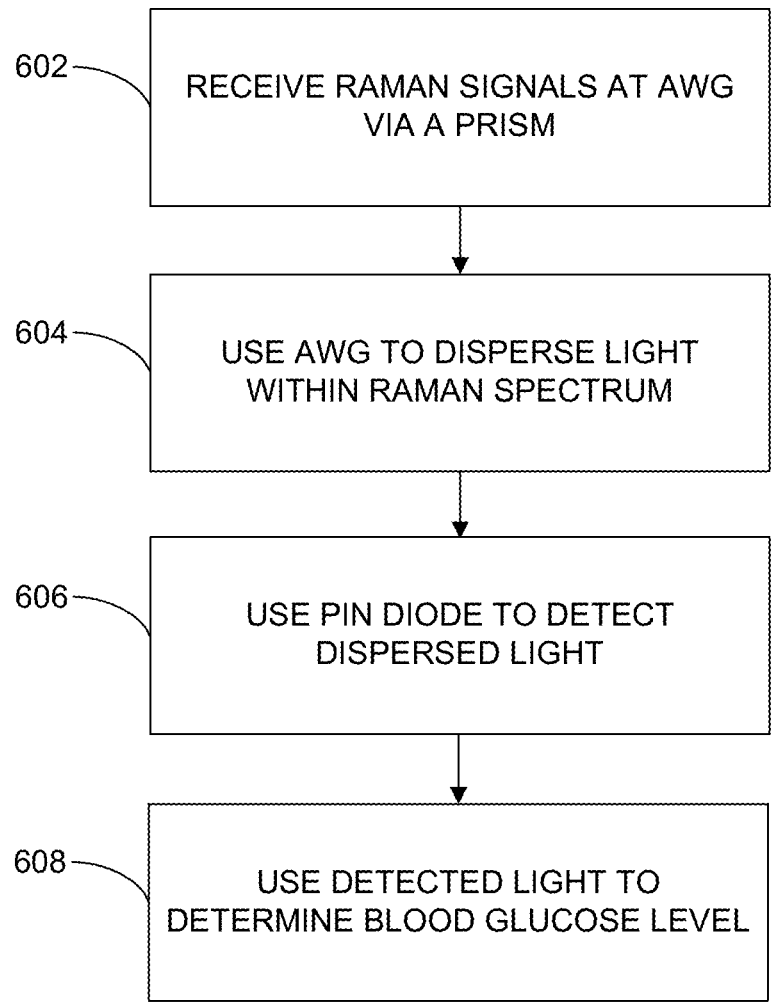
FIG. 6 is a flowchart of an illustrative process for monitoring glucose by using an AWG-based micro-Raman spectrometer in accordance with various embodiments of the present disclosure.

FIG. 6 is a flowchart of an illustrative process for monitoring glucose by using an AWG-based micro-Raman spectrometer in accordance with various embodiments of the present disclosure.

At step 602, an AWG receives Raman signals that may be caused by a laser, e.g., a diode laser. In embodiments, the Raman signals are received via a prism that is coupled to the AWG. The AWG may comprise waveguides that have been formed by filing a set of trenches in a substrate.

At step 604, the AWG may be used to disperse light within a Raman spectrum.

At step 606, the dispersed light is detected by a PIN diode that has been formed by filing a second set of trenches in the substrate.

At step 608, some or all of the detected light is used to determine a blood glucose level, e.g., by measuring a fingerprint from which blood glucose molecules may be identified.

Figure 7:
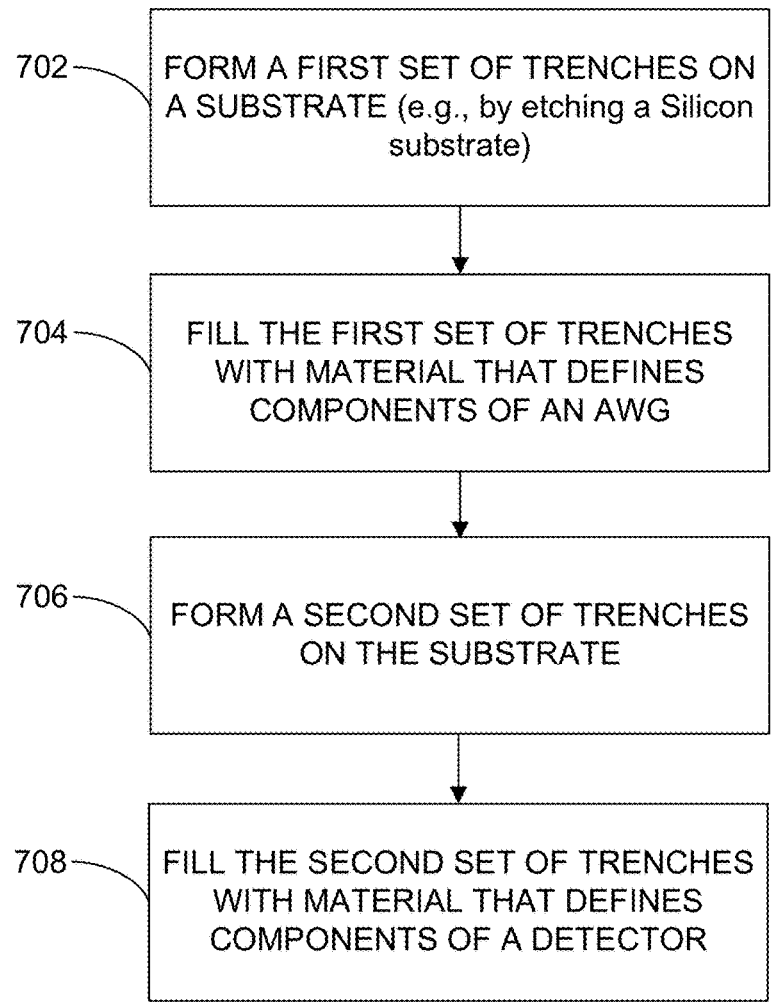
FIG. 7 is a flowchart of an illustrative process for producing an AWG-based micro-Raman spectrometer in accordance with various embodiments of the present disclosure.

FIG. 7 is a flowchart of an illustrative process for producing an AWG-based micro-Raman spectrometer in accordance with various embodiments of the present disclosure.

At step 702, a first set of trenches is formed on a substrate. This may be accomplished, e.g., by etching a trench into a Silicon substrate using any known semiconductor processing process in the art.

At step 704, the trenches are filled with material that defines one or more components of an AWG. It is understood that the AWG may comprise any number of core and cladding materials.

At step 706, a second set of trenches is formed on the substrate.

At step 708, the trenches formed at step 706 are filled with material that defines components of a detector, e.g., a PIN diode that may be used as a photo detector.

It is understood that part of all of the first and second set of trenches may be simultaneously formed and/or filled. It will be appreciated to those skilled in the art that the preceding examples and embodiment are exemplary and not limiting to the scope of the present invention. It is intended that all permutations, enhancements, equivalents, combinations, and improvements thereto that are apparent to those skilled in the art upon a reading of the specification and a study of the drawings are included within the true spirit and scope of the present invention.

What is claimed is:

1. An opto-electronic circuit for an Arrayed Waveguide Grating (AWG)-based Raman spectrometer for non-invasive optical glucose monitoring, the opto-electronic circuit comprising:
    an AWG, comprising:
        a substrate;
        filled waveguide trenches on the substrate comprising an optical waveguide;
        filled doped trenches on the substrate comprising a detector;
    a laser source configured to shine light at human skin;
    a prism configured to capture light scattered off the human skin when exposed to light from the laser source ("detected light") and to direct the light toward the AWG;
    a signal processing device coupled to the detector;
    wherein the signal processing device is configured to determine a glucose level based on the output of the detector.

2. The spectrometer according to claim 1, wherein the detector is a PIN diode that serves as a photo detector.

3. The spectrometer according to claim 1, wherein the AWG is configured to receive scattered light within a wavelength range that corresponds to Raman scattering spectrum.

4. The spectrometer according to claim 1, wherein at least some components of the AWG are made using semiconductor processing materials and one or more trenches are formed by a dry etch process.

5. The spectrometer according to claim 1, wherein the filled waveguide trenches comprise undoped regions.

6. The spectrometer according to claim 1, wherein the filled waveguide trenches are filled with core and cladding materials.

7. The spectrometer according to claim 1, further comprising a storage device comprising a capacitor to collect photoelectrons that are generated by the detector.

8. The spectrometer according to claim 1, wherein the optical waveguide comprises a waveguide core material and a waveguide cladding material.

9. A method for non-invasive optical glucose monitoring using Arrayed Waveguide Grating (AWG)-based Raman spectrometer, the method comprising:
    receiving at an AWG a light within a Raman spectrum, wherein:
        the AWG comprises:
            a substrate;
            filled waveguide trenches on the substrate comprising an optical waveguide; and
            filled doped trenches on the substrate comprising a detector; and
        the light is light from a laser source that is scattered off human skin and directed by a prism toward the AWG;
    detecting, at the detector, light dispersed by the AWG; and
    using a signal processing device coupled to the detector to determine a glucose level based on the output of the detector.

10. The method according to claim 9, wherein determining the glucose level comprises identifying, based on the dispersed light, one or more wavelengths that are characteristic for glucose molecules.

11. A method for producing an Arrayed Waveguide Grating (AWG)-based Raman spectrometer, die method comprising:
    forming a first set of trenches on a substrate;
    filling the first set of trenches with first material that at least partially defines optical waveguides of an AWG, the first set of trenches serving as intrinsic regions of PIN diodes;
    forming a second set of trenches on a substrate;
    filling the second set of trenches with a second material that at least partially defines doped regions of the PIN diodes;
    electrically connecting the PIN diodes in a manner to facilitate the detection of photons; and
    integrating the optical waveguides of the AWG and the second set of trenches so as to form individual PIN diodes.

12. The method according to claim 11, further comprising arranging the individual PIN diodes and the AWG on a same plane on a die.

* * * * *